US012195463B2

(12) United States Patent
Li et al.

(10) Patent No.: US 12,195,463 B2
(45) Date of Patent: Jan. 14, 2025

(54) ORGANIC COMPOUNDS

(71) Applicant: INTRA-CELLULAR THERAPIES, INC., New York, NY (US)

(72) Inventors: Peng Li, New Milford, NJ (US); Kimberly Vanover, New York, NY (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 805 days.

(21) Appl. No.: 17/416,997

(22) PCT Filed: Dec. 20, 2019

(86) PCT No.: PCT/US2019/067902
§ 371 (c)(1),
(2) Date: Jun. 21, 2021

(87) PCT Pub. No.: WO2020/132474
PCT Pub. Date: Jun. 25, 2020

(65) Prior Publication Data
US 2022/0056031 A1 Feb. 24, 2022

Related U.S. Application Data

(60) Provisional application No. 62/783,685, filed on Dec. 21, 2018.

(51) Int. Cl.
*C07D 471/16* (2006.01)
*A61P 25/00* (2006.01)

(52) U.S. Cl.
CPC ............ *C07D 471/16* (2013.01); *A61P 25/00* (2018.01)

(58) Field of Classification Search
CPC ............................... C07D 471/16; A61P 25/00
See application file for complete search history.

(56) References Cited

U.S. PATENT DOCUMENTS

| | | |
|---|---|---|
| 4,238,607 A | 12/1980 | Rajagopalan |
| 4,849,246 A | 7/1989 | Schmidt |
| 5,114,976 A | 5/1992 | Norden |
| 5,151,419 A | 9/1992 | Perenyi et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,849,619 B2 | 2/2005 | Robichaud et al. |
| 6,849,640 B2 | 2/2005 | Ennis et al. |
| 7,071,186 B2 | 7/2006 | Robichaud et al. |
| 7,081,455 B2 | 7/2006 | Robichaud et al. |
| 7,183,282 B2 | 2/2007 | Robichaud et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,998,971 B2 | 8/2011 | Barlow et al. |
| 8,309,722 B2 | 11/2012 | Tomesch et al. |
| 8,461,148 B2 | 6/2013 | Hollander |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,791,138 B2 | 7/2014 | Seeman et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,118,926 B2 | 11/2018 | Koolman et al. |
| 10,221,176 B2 | 3/2019 | Tomesch et al. |
| 10,245,260 B2 * | 4/2019 | Yao .......................... A61P 25/00 |
| 10,322,134 B2 | 6/2019 | Vanover et al. |
| 10,363,220 B2 | 7/2019 | Li |

(Continued)

FOREIGN PATENT DOCUMENTS

GB 1476087 6/1977

OTHER PUBLICATIONS

Kudla, et al., "Influence of G protein-biased agonists of μ-opioid receptor on addiction-related behaviors," *Pharmacol Rep.*, 73(4), pp. 1033-1051, (2021).
Torralva, et al., "Fentanyl but not Morphine Interacts with Nonopioid Recombinant Human Neurotransmitter Receptors and Transporters," *J Pharmacol Exp Ther.*, 374(3), pp. 376-391, (2020).
Balbach, S., et al., "Pharmaceutical evaluation of early development candidates 'the 100 mg-approach'", International Journal of Pharmaceutics, vol. 275, p. 1-12 (2004).
Bremner et al., "Neuroimaging of Posttraumatic Stress Disorder", Psychiatric Annals Journal, vol. 28, Issue 8, p. 445-450, (1998).
Byrn, S., et al., "Pharmaceutical Solids: A Strategic Approach to Regulatory Considerations", Pharmaceutical Research, vol. 12, No. 7, p. 945-954 (1995).
Caira, et al., "Crystalline Polymorphism of Organic Compounds," Topics in Current Chemistry, vol. 198, p. 163-203, (1998).

(Continued)

*Primary Examiner* — Matthew P Coughlin
*Assistant Examiner* — Quincy McKoy
(74) *Attorney, Agent, or Firm* — Hoxie & Associates LLC

(57) ABSTRACT

The invention relates to a particular enantiomer of a substituted heterocycle fused gamma-carboline, in free, solid, pharmaceutically acceptable salt and/or substantially pure form as described herein, pharmaceutical compositions thereof, and methods of use in the treatment of diseases involving the 5-HT$_{2A}$ receptor, and pathways involving the dopamine D$_1$ and D$_2$ receptor signaling system.

14 Claims, No Drawings

(56) References Cited

U.S. PATENT DOCUMENTS

| | | |
|---|---|---|
| 10,533,015 B1 | 1/2020 | Tusche et al. |
| 10,654,854 B2 | 5/2020 | Li et al. |
| 10,688,097 B2 | 6/2020 | Yao et al. |
| 10,716,786 B2 | 7/2020 | Li et al. |
| 10,799,500 B2 | 10/2020 | Yao et al. |
| 10,906,906 B2 | 2/2021 | Li et al. |
| 10,961,245 B2 | 3/2021 | Li et al. |
| 11,014,925 B2 | 5/2021 | Li et al. |
| 11,053,245 B2 | 7/2021 | Mates et al. |
| 11,124,514 B2 | 9/2021 | Mates et al. |
| 11,376,249 B2 | 7/2022 | Li et al. |
| 11,427,587 B2 | 8/2022 | Li et al. |
| 11,773,095 B2 | 10/2023 | Li et al. |
| 11,844,757 B2 | 12/2023 | Yao et al. |
| 2005/0222209 A1 | 10/2005 | Zeldis et al. |
| 2011/0269777 A1 | 11/2011 | Bachurin et al. |
| 2016/0159787 A1 | 6/2016 | Linz et al. |
| 2016/0354315 A1 | 12/2016 | Li |
| 2020/0392135 A1 | 12/2020 | Wennogle et al. |
| 2021/0009592 A1 | 1/2021 | Li et al. |
| 2021/0093634 A1 | 4/2021 | Snyder et al. |
| 2021/0145829 A1 | 5/2021 | Li et al. |
| 2021/0163481 A1 | 6/2021 | Li et al. |
| 2022/0048910 A1 | 2/2022 | Li et al. |
| 2022/0056030 A1 | 2/2022 | Li et al. |
| 2022/0160704 A2 | 5/2022 | Torralva |
| 2022/0184072 A1 | 6/2022 | Davis et al. |

OTHER PUBLICATIONS

Darmani, N. A., et al., "Do Functional Relationships Exist Between 5-HT1A and 5-HT2 Receptors?" Pharmacology and Biochemistry & Behavior, vol. 36, p. 901-906, (1990).

Harbert, C.A. et al., "Neuroleptic Activity in 5-Aryltetrahydro-y-carbolines", J. Med. Chem., vol. 23, pp. 635-643 (1980).

Kay, S.R., et al., "The Positive and Negative Syndrome Scale (PANSS) for Schizophrenia," Schizophrenia Bulletin, vol. 13, Issue 2, pp. 261-276, (1987).

Kessler, R.C., et al., "Lifetime Prevalence and Age-of-Onset Distributions of DSM-IV Disorders in the National Comorbidity Survey Replication", Arch Gen Psychiatry, vol. 62, pp. 593-602, (2005).

Lee, T., et al. "Novel, Highly Potent, Selective 5-HT2A/D2 Receptor Antagonists as Potential Atypical Antipsychotics," Bioorg. Med. Chem. Lett., vol. 13, pp. 767-770, (2003).

Lieberman, J.A., et al., "ITI-007 for the Treatment of Schizophrenia: A 4-Week Randomized, Double-Blind, Controlled Trial," Biol. Psychiatry, 79(12), pp. 952-961, (2015).

Marek, G.J., et al., "Synergistic Action of 5-$HT_{2A}$ Antagonists and Selective Serotonin Reuptake Inhibitors in Neuropsychiatric Disorder," Neuropsychopharmacology, (2003), vol. 28, pp. 402-412.

Pine, A. et al., "Dopamine, Time, and Impulsivity in Human," Journal of Neuroscience, vol. 30, No. 26, 8888-8896 (2010).

Press Release, "Intra-Cellular Therapies Announces Additional Results from Phase 1/11 Clinical Trial for ITI-007 in Healthy Geriatric Subjects and Patients With Dementia," Intra- Cellular Therapies, Press Release Date: Nov. 21, 2014, (http://ir.intracellulartherapies.com/releasedetail.cfm?ReleaseID=8 84325), accessed on May 31, 2016.

PubChem, Open Chemistry Database, Compound Summary for CID-22036753, pp. 4, (2007), 12 pages.

PubChem, Open Chemistry Database, PubChem CID 90655118, (2012), 2 pages.

PubChem, Open Chemistry Database, PubChem SID 103920954, PubChem CID 69873532, (2011 ), 6 pages.

PubChem, Open Chemistry Database, Compound Summary for SID 103920954 (2011) 6 pages.

Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.

Angst et al. "Prevalence and Characteristics of Undiagnosed Bipolar Disorders in Patients With a Major Depressive Episode", Arch Gen Psychiatry, vol. 68(8), p. 701-709, (2011).

Davis et al., "ITI-007 in the treatment of schizophrenia: from novel pharmacology to clinical outcomes," Expert Review of Neurotherapeutics, vol. 16, No. 6, pp. 601-614 (2016).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Davis, et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.

Gramigna, J, "Lumateperone Safe, Effective for Depressive Symptoms Among Patients with Bipolar Disorders," American Society of Clinical Psychopharmacology Annual Meeting, Jun. 2, 2020, 3 pages.

Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.

Khorana, N., et al., "Gamma-Carbolines: Binding at 5-HT5A Serotonin Receptors", Bioorganic & Medicinal Chemistry, vol. 11, pp. 717-722, p. 718 Table 1, (2003).

Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).

Noble, F., et al., "The opioid receptors as targets for drug abuse medication," British Journal of Psychology, vol. 172, pp. 3964-3979, (2015).

Perlis, R.H., et al., "Clinical Features of Bipolar Depression Versus Major Depressive Disorder in Large Multicenter Trials," Am J Psychiatry, vol. 163, (2006), pp. 225-231.

Pubchem, CID-9953107, p. 3, pp. 1-9 (2006).

Renner, J.A., Jr., "Management of Psychiatric Medications in Patients Receiving Buprenorphine/Naloxone," PCSS MAT Training Providers' Clinical Support System for Medical Assisted Treatment, Last Updated: Nov. 28, 2013, 4 pages.

Snyder, G.L., et al., "Functional profile of a novel modulator of serotonin, dopamine, and glutamate neurotransmission," Psychopharmacology, vol. 232, p. 605-621 (2015) Published online Aug. 2014, DOI 10.1007/s00213-014-3704-1.

Vanover, et al., "Dopamine D2 receptor occupancy of lumateperone (ITI-007): a Positron Emission Tomography Study in patients with schizophrenia," Neuropsychopharmacology 44:598-605, (2019).

Vanover, K., et al., "ITI-007: A Novel Therapy for the Treatment of Schizophrenia and Related Psychoses," International Clinical Psychopharamcology, vol. 26, e56, 1 page, (2011).

Zhang, G., et al., "The role of serotonin 5-$HT_{2A}$ receptors in memory and cognition," frontiers in Pharmacology, vol. 6, Article 225, (2015).

* cited by examiner

ORGANIC COMPOUNDS

CROSS-REFERENCE TO RELATED APPLICATIONS

This application is a U.S. National Stage application under 35 U.S.C. § 371 of International Application No. PCT/US2019/067902, filed on Dec. 20, 2019, which claims priority to and the benefit of U.S. Provisional Application No. 62/783,685, filed on Dec. 21, 2018, the contents of each of which are hereby incorporated by reference in their entireties.

FIELD OF THE INVENTION

The invention relates to a particular substituted heterocycle fused gamma-carboline, in free, solid, pharmaceutically acceptable salt and/or substantially pure form as described herein, pharmaceutical compositions thereof, and methods of use in the treatment of diseases involving the $5\text{-HT}_{2A}$ receptor, and pathways involving dopamine $D_1$ and/or $D_2$ receptor signaling systems, e.g., diseases or disorders such as anxiety, psychosis, schizophrenia, sleep disorders, sexual disorders, social phobias, depression and mood disorders, such as those associated with psychosis or Parkinson's disease; psychosis such as schizophrenia associated with depression; bipolar disorder; substance use disorders, substance abuse disorders, drug dependencies, such as cocaine and amphetamine dependency, drug withdrawal symptoms; obsessive-compulsive disorder (OCD), obsessive-compulsive personality disorder (OCPD), and related disorders; and other psychiatric and neurological conditions, as well as to combinations with other agents.

BACKGROUND OF THE INVENTION

Substituted heterocycle fused gamma-carbolines are known to be agonists or antagonists of $5\text{-HT}_2$ receptors, particularly $5\text{-HT}_{2A}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with $5\text{-HT}_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. U.S. Pat. Nos. 8,309,722, and 7,081,455, also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, U.S. Pat. No. 8,598,119 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize $5\text{-HT}_{2A}$ receptors without affecting or minimally affecting dopamine $D_2$ receptors, thereby useful for the treatment of sleep disorders without the side effects associated with high occupancy of the dopamine $D_2$ pathways or side effects of other pathways (e.g., $GABA_A$ receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains. U.S. Pat. No. 8,648,077 also discloses methods of preparing toluenesulfonic acid addition salt crystals of these substituted heterocycle fused gamma-carbolines.

One particular fused heterocycle gamma carboline, 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, is disclosed in, for example, US 2011/0071080, US 2015/0072964, US 2015/0080404, and US 2016/0310503. This compound is a potent serotonin $5\text{-HT}_{2A}$ receptor antagonist, dopamine receptor D1 and D2 modulator, and serotonin transporter (SERT) antagonist.

Recent evidence shows that this compound may also operate, in part, through NMDA receptor antagonism via mTOR1 signaling, in a manner similar to that of ketamine. Ketamine is a selective NMDA receptor antagonist. Ketamine acts through a system that is unrelated to the common psychogenic monoamines (serotonin, norepinephrine and dopamine), and this is a major reason for its much more rapid effects. Ketamine directly antagonizes extrasynaptic glutamatergic NMDA receptors, which also indirectly results in activation of AMPA-type glutamate receptors. The downstream effects involve the brain-derived neurotrophic factor (BDNF) and mTORC1 kinase pathways. Compounds related to those of the present disclosure also influence NMDA and AMPA receptor signaling, albeit indirectly (in contrast to ketamine's direct action). Similar to the effects produced by ketamine, recent evidence suggests that these compounds enhance both NMDA and AMPA-induced currents in rat medial prefrontal cortex pyramidal neurons via activation of D1 receptors, and that this is associated with increased mTORC1 signaling. International application PCT/US2018/043100 discloses such effects for certain substituted fused heterocycle gamma-carbolines, and useful therapeutic indications related thereto.

4-(6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone has also recently completed or is undergoing Phase III clinical trials for the treatment of schizophrenia, agitation associated with dementia, and bipolar depression. It is expected to gain regulatory approval for schizophrenia in the near future.

The publication US 2017/319580 discloses additional novel fused heterocycle gamma carbolines. These new compounds were found to display serotonin receptor inhibition, SERT inhibition, and dopamine receptor modulation. However, these compounds were also unexpectedly found to show significant activity at mu-opiate receptors.

The Compound of Formula A, shown below, is disclosed in US 2017/319580. This compound is a potent serotonin $5\text{-HT}_{2A}$ receptor antagonist and mu-opiate receptor partial agonist or biased agonist. This compound also interacts with dopamine receptors, and in particular the dopamine D1 receptors, but it has only weak SERT antagonism activity.

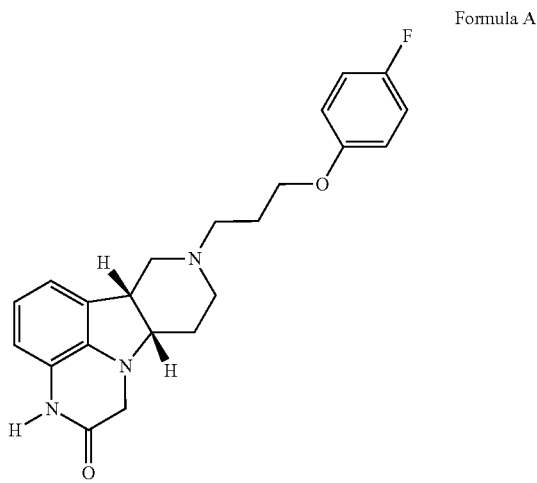 [SMILES: O=C1CN2c3c(cccc3[C@@H]3CN(CCCOc4ccc(F)cc4)CC[C@@H]32)N1]

Formula A

It is also believed that the Compound of Formula A, via its D1 receptor activity, may also enhance NMDA and AMPA mediated signaling through the mTOR pathway. The Compound of Formula A is thus useful for the treatment or prophylaxis of central nervous system disorders.

BRIEF SUMMARY

In a first aspect, the present disclosure relates to a compound (Compound I) of Formula I:

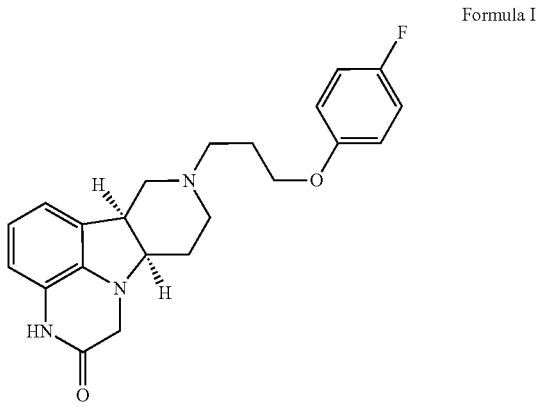 [SMILES: O=C1CN2c3c(cccc3[C@H]3CN(CCCOc4ccc(F)cc4)CC[C@H]32)N1]

Formula I in free or salt form (e.g., pharmaceutically acceptable salt form), for example in an isolated or purified free or salt form (e.g., pharmaceutically acceptable salt form).

The present disclosure provides additional exemplary embodiments of the Compound of Formula I, in free or salt form (e.g., pharmaceutically acceptable salt form), for example in an isolated or purified free or salt form (e.g., pharmaceutically acceptable salt form), including:

1.1 Compound I, wherein the compound is in free form (free base form);
1.2 Compound I, wherein the compound is in salt form;
1.3 Compound I, wherein the compound is in pharmaceutically acceptable salt form;
1.4 Compound I, wherein the compound is in acid addition salt form, for example, hydrochloric or toluenesulfonic acid salt form;
1.5 Compound I, or any of 1.1-1.4, in substantially pure diastereomeric form (i.e., substantially free from other diastereomers, including enantiomers);
1.6 Compound I or any of 1.1-1.4, having a diastereomeric excess of greater than 70%, preferably greater than 80%, more preferably greater than 90% and most preferably greater than 95%;
1.7 Compound I or any of 1.1-1.6 in solid form, e.g., in crystal form;
1.8 Compound I or any of 1.1-1.6, in isolated or purified form (e.g., in at least 90% pure form, or at least 95% or at least 98% or at least 99%);

The compound of Formula A is a highly potent serotonin receptor antagonist ($K_i \leq 10$ nM), and is a potent D1 receptor modulator ($K_i \leq 50$ nM) but a weak D2 receptor modulator ($K_i \leq 160$ nM). The compound of Formula A is also a potent mu opiate receptor ligand ($K_i \leq 11$ nM) but is inactive at SERT ($K_i \leq 600$ nM).

It has now been surprisingly found that the compound of Formula I, which is the enantiomer of the compound of Formula A, has no SERT activity, moderately strong D1 receptor binding and serotonin receptor inhibition, and only weak mu receptor activity. To put this in perspective, the binding affinity for the compounds of Formula I and Formula A may be qualitatively compared as follows:

Formula A: $5\text{-}HT_{2A}\sim Mu > D1 > D2 >> SERT$

Formula I: $D1 > 5\text{-}HT_{2A} > D2 > Mu >>> SERT$

Thus, the compound of Formula A has similar potency for $5\text{-}HT_{2A}$ and Mu, but significantly weaker D1 and D2 binding and very little SERT binding. In contrast, to the compound of Formula A, the compound of Formula I is most active at the D1 receptor, followed by the $5\text{-}HT_{2A}$ receptor, with weak D2 affinity, minimal mu receptor activity and no SERT activity. While it is well known for enantiomers of pharmacologically active compounds to have different or opposite activities, such as one enantiomer being active and the other enantiomer being non-active, it is unexpected and unpredictable that the compound of Formula I would have similar activity to its enantiomer, the compound of Formula A, at only the D1 and D2 receptors, yet very different relative activity at the $5\text{-}HT_{2A}$, SERT and mu-opiate receptors. Moreover, the pharmacological profile of the compound of Formula I is also quite unexpectedly different than 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone.

This unexpected activity profile provides new avenues for the treatment of disease based on this relatively enhanced pharmacologic activity at the D1 and $5\text{-}HT_{2A}$ receptors, with weaker D2 receptor activity.

In a second aspect, the present disclosure provides a pharmaceutical composition (Pharmaceutical Composition I) comprising a compound according to any one of Compound of Formula I or 1.1-1.8, e.g., in admixture with a pharmaceutically acceptable diluent or carrier. In a particular embodiment, the Compound of Formula I or any of 1.1-1.8 is in pharmaceutically acceptable salt form.

In a further embodiment, the Pharmaceutical Compositions of the present disclosure, are for a sustained or delayed release formulation (Pharmaceutical Composition 1-A), e.g., a depot formulation. In some embodiments, the Compound of Formula I or any of 1.1-1.8 is provided, preferably in free or pharmaceutically acceptable salt form, in admixture with a pharmaceutically acceptable diluent or carrier, in the form of an injectable depot, which provides sustained or delayed release of the compound.

In a particular embodiment, the Pharmaceutical Composition 1-A comprises a compound according to any one of Compound I or 1.1-1.8, in free base or pharmaceutically acceptable salt form, optionally in crystal form, wherein the compound has been milled to, or the compound crystallized to, microparticle or nanoparticle size, e.g., particles or crystals having a volume-based particle size (e.g., diameter or Dv50) of 0.5 to 100 microns, for example, for example, 5-30 microns, 10-20 microns, 20-100 microns, 20-50 microns or 30-50 microns. Such particles or crystals may be combined with a suitable pharmaceutically acceptable diluent or carrier, for example water, to form a depot formulation for injection. For example, the depot formulation may be formulated for intramuscular or subcutaneous injection with a dosage of drug suitable for 4 to 6 weeks of treatment. In some embodiments, the particles or crystals have a surface area of 0.1 to 5 $m^2/g$, for example, 0.5 to 3.3 $m^2/g$ or from 0.8 to 1.2 $m^2/g$.

In another embodiment, the present disclosure provides a Pharmaceutical Composition I-B, which is Pharmaceutical Composition I, wherein the Compound of Formulas I et seq. is in a polymeric matrix. In one embodiment, the Compound of the present disclosure is dispersed or dissolved within the polymeric matrix. In a further embodiment, the polymeric matrix comprises standard polymers used in depot formulations such as a polyester of a hydroxyfatty acid and derivatives thereof, or a polymer of an alkyl alpha-cyanoacrylate, a polyalkylene oxalate, a poly-ortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide).

The Pharmaceutical Composition I-B is particularly useful for sustained or delayed release, wherein the Compound of the present disclosure is released upon degradation of the polymeric matrix. These Compositions may be formulated for controlled- and/or sustained-release of the Compounds of the present disclosure (e.g., as a depot composition) over a period of up to 180 days, e.g., from about 14 to about 30 to about 180 days. For example, the polymeric matrix may degrade and release the Compounds of the present disclosure over a period of about 30, about 60 or about 90 days. In another example, the polymeric matrix may degrade and release the Compounds of the present disclosure over a period of about 120, or about 180 days.

In still another embodiment, the Pharmaceutical Composition I or I-A or I-B may be formulated for administration by injection, for example, as a sterile aqueous solution.

In another embodiment, the present disclosure provides a Pharmaceutical Composition (Pharmaceutical Composition I-C) comprising a Compound of Formulas I et seq. as hereinbefore described, in an osmotic controlled release oral delivery system (OROS), which is described in US 2001/0036472 and US 2009/0202631, the contents of each of which applications are incorporated by reference in their entirety. Therefore in one embodiment, the present disclosure provides a pharmaceutical composition or device comprising (a) a gelatin capsule containing a Compound of any of Formulae I et seq. in free or pharmaceutically acceptable salt form, optionally in admixture with a pharmaceutically acceptable diluent or carrier; (b) a multilayer wall superposed on the gelatin capsule comprising, in outward order from the capsule: (i) a barrier layer, (ii) an expandable layer, and (iii) a semipermeable layer; and (c) and orifice formed or formable through the wall (Pharmaceutical Composition P.1).

In another embodiment, the invention provides a pharmaceutical composition comprising a gelatin capsule containing a liquid, the Compound of Formulas I et seq. in free or pharmaceutically acceptable salt form, optionally in admixture with a pharmaceutically acceptable diluent or carrier, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall (Pharmaceutical Composition P.2).

In still another embodiment, the invention provides a composition comprising a gelatin capsule containing a liquid, the Compound of Formulas I et seq. in free or pharmaceutically acceptable salt form, optionally in admixture with a pharmaceutically acceptable diluent or carrier, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice (Pharmaceutical Composition P.3).

In still another embodiment, the invention provides a composition comprising a gelatin capsule containing a liquid, the Compound of Formulas I et seq. in free or pharmaceutically acceptable salt form, optionally in admixture with a pharmaceutically acceptable diluent or carrier, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use (Pharmaceutical Composition P.4). The expandable layer may be formed in one or more discrete sections, such as for example, two sections located on opposing sides or ends of the gelatin capsule.

In a particular embodiment, the Compound of the present disclosure in the Osmotic-controlled Release Oral Delivery System (i.e., in Composition P.1-P.4) is in a liquid formulation, which formulation may be neat, liquid active agent, liquid active agent in a solution, suspension, emulsion or self-emulsifying composition or the like.

Further information on Osmotic-controlled Release Oral Delivery System composition including characteristics of the gelatin capsule, barrier layer, an expandable layer, a semi-permeable layer; and orifice may be found in US 2001/0036472, the contents of which are incorporated by reference in their entirety.

Other Osmotic-controlled Release Oral Delivery System for the Compound of Formulas I et seq. or the Pharmaceutical Composition of the present disclosure may be found in US 2009/0202631, the contents of which are incorporated by reference in their entirety. Therefore, in another embodiment, the invention provides a composition or device comprising (a) two or more layers, said two or more layers comprising a first layer and a second layer, said first layer comprises the Compound of Formulas I et seq., in free or pharmaceutically acceptable salt form, optionally in admixture with a pharmaceutically acceptable diluent or carrier, said second layer comprises a polymer; (b) an outer wall surrounding said two or more layers; and (c) an orifice in said outer wall (Pharmaceutical Composition P.5).

Pharmaceutical Composition P.5 preferably utilizes a semi-permeable membrane surrounding a three-layer-core: in these embodiments, the first layer is referred to as a first drug layer and contains low amounts of drug (e.g., the Compound of Formulas I et seq.) and an osmotic agent such as salt, the middle layer referred to as the second drug layer contains higher amounts of drug, excipients and no salt; and the third layer referred to as the push layer contains osmotic agents and no drug (Pharmaceutical Composition P.6). At least one orifice is drilled through the membrane on the first drug layer end of the capsule-shaped tablet.

Pharmaceutical Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof (Pharmaceutical Composition P.7). Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers.

In a particular embodiment, the invention provides Pharmaceutical Composition P.7 wherein the first drug layer comprises salt and the second drug layer contains no salt. Pharmaceutical Composition P.5-P.7 may optionally comprise a flow-promoting layer between the membrane and the drug layers.

Pharmaceutical Compositions P.1-P.7 will generally be referred to as Osmotic-controlled Release Oral Delivery System Composition.

In a third aspect, the invention provides a method (Method 1) for the treatment or prophylaxis of a central nervous system disorder, comprising administering to a patient in need thereof a Compound of Formula I et seq. or a Pharmaceutical Composition I, I-A, I-B, I-C, or any of P.1-P.7. In particular embodiments, Method 1 comprises administering:

1.1 Compound I or any of 1.1-1.8, in free form;
1.2 Compound I or any of 1.1-1.8, in pharmaceutically acceptable salt form;
1.3 Compound I or any of 1.1-1.8, in acid addition salt form;
1.4 Pharmaceutical Composition I;
1.5 Any of Pharmaceutical Compositions I-A, I-B or I-C;
1.6 Any of Pharmaceutical Composition P.1 to P.7; or
1.7 Any Osmotic-controlled Release Oral Delivery System Composition as hereinbefore described.

In a further embodiment of the third aspect, the present disclosure provides Method 1 or any of Methods 1.1-1.7, wherein the method is further as described as follows:

1.8 Method 1 or any of Methods 1.1-1.7, wherein the central nervous system disorder is a disorder selected from a group consisting of obesity, anxiety (including general anxiety, social anxiety, and panic disorders), depression (for example refractory depression and MDD), psychosis (including psychosis associated with dementia, such as hallucinations in advanced Parkinson's disease or paranoid delusions), schizophrenia, sleep disorders (particularly sleep disorders associated with schizophrenia and other psychiatric and neurological diseases), sexual disorders, agoraphobia, social phobias, agitation in dementia (e.g., agitation in Alzheimer's disease), agitation in autism and related autistic disorders, gastrointestinal disorders such as dysfunction of the gastrointestinal tract motility, and dementia, for example dementia of Alzheimer's disease or of Parkinson's disease; mood disorders; substance use disorder and/or substance abuse disorder; drug dependencies, for example, cocaine dependency and/or amphetamine dependency, and withdrawal from drug dependency (e.g., cocaine or amphetamine dependency); co-morbidities associated with drug dependencies, such as depression, anxiety and psychosis; binge eating disorder; and obsessive-compulsive disorder (OCD), obsessive-compulsive personality disorder (OCPD) and related disorders; or stimulant use disorder (SUD);

1.9 Method 1 or any of Methods 1.1-1.8, wherein the central nervous system disorder is a disorder involving serotonin 5-HT$_2$A, dopamine D1 and/or D2 receptor system pathways as similarly described in US 2011/071080, the contents of which are herein incorporated by reference in their entirety;

1.10 Method 1 or any of Methods 1.1-1.9, wherein the central nervous system disorder is a disorder selected from the following: (1) psychosis, e.g., schizophrenia, in a patient suffering from depression; (2) depression in a patient suffering from psychosis, e.g., schizophrenia; (3) mood disorders associated with psychosis and/or drug dependencies, e.g., schizophrenia or Parkinson's disease; (4) sleep disorders associated with psychosis, e.g., schizophrenia or Parkinson's disease; and (5) substance addiction, substance use disorders and/or substance-induced disorders, optionally wherein the patient suffers from residual symptoms of anxiety or anxiety disorder; and optionally wherein the depression is treatment-resistant depression;

1.11 Method 1 or any of Methods 1.1-1.9, wherein the central nervous system disorder is psychosis, e.g., schizophrenia and said patient is a patient suffering from depression;

1.12 Method 1 or any of Methods 1.1-1.11, wherein said patient is unable to tolerate the side effects of conventional antipsychotic drugs, e.g., chlorpromazine, haloperidol, droperidol, fluphenazine, loxapine, mesoridazine molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone and ziprasidone;

1.13 Method 1 or any of Methods 1.1-1.12, wherein said patient is unable to tolerate the side effects of conventional antipsychotic drugs, e.g., haloperidol, brexpiprazole, cariprazine, asenapine, lurasidone, aripiprazole, clozapine, olanzapine, quetiapine, risperidone, and ziprasidone;

1.14 Method 1 or any of Methods 1.1-1.10, wherein said disorder is depression and said patient is a patient suffering from psychosis, e.g., schizophrenia, or Parkinson's disease;

1.15 Method 1 or any of Methods 1.1-1.10, wherein said disorder is sleep disorder and said patient is suffering from depression;

1.16 Method 1 or any of Methods 1.1-1.10, wherein said one or more disorders is sleep disorder and said patient is suffering from psychosis, e.g., schizophrenia;

1.17 Method 1 or any of Methods 1.1-1.10, wherein said one or more disorders is sleep disorder and said patient is suffering from Parkinson's disease;

1.18 Method 1 or any of Methods 1.1-1.10, wherein said one or more disorders is sleep disorder and said patient is suffering from depression and psychosis, e.g., schizophrenia, or Parkinson's disease.

1.19 Method 1 or any of 1.1-1.18, wherein said patient is suffering from a drug dependency disorder, optionally in conjunction with any preceding disorders, for example, wherein said patient suffers from a drug dependency, e.g. a stimulant dependency, such as cocaine dependency or amphetamine dependency, and optionally wherein the patient suffers from a co-morbidity, such as anxiety, depression or psychosis, or residual symptoms of anxiety or anxiety disorder and/or altered mood (e.g., depression); further optionally wherein the patient suffers from an opiate overdose;

1.20 Any of the foregoing methods, wherein the effective amount is 1 mg-1000 mg, for example 2.5 mg-50 mg, or for a long-acting formulation, 25 mg-1500 mg, for example, 50 mg to 500 mg, or 250 mg to 1000 mg, or 250 mg to 750 mg, or 75 mg to 300 mg;

1.21 Any of the foregoing methods, wherein the effective amount is 1 mg-100 mg per day, for example 2.5 mg-50 mg per day, or 10 to 100 mg per day;

1.22 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

1.23 Any of the foregoing methods wherein the patient suffers from Parkinson's disease.

1.24 Any of the foregoing methods wherein the patient undergoes concurrent or consecutive treatment with Lumateperone and/or the compound of Formula A.

Substance-use disorders and substance-induced disorders are the two categories of substance-related disorders defined by the Fifth Edition of the DSM (the Diagnostic and Statistical Manual of Mental Disorders, DSM-5). A substance-use disorder is a pattern of symptoms resulting from use of a substance which the individual continues to take, despite experiencing problems as a result. A substance-induced disorder is a disorder induced by use if the substance. Substance-induced disorders include intoxication, withdrawal, substance induced mental disorders, including substance induced psychosis, substance induced bipolar and related disorders, substance induced depressive disorders, substance induced anxiety disorders, substance induced obsessive-compulsive and related disorders, substance induced sleep disorders, substance induced sexual dysfunctions, substance induced delirium and substance induced neurocognitive disorders.

The DSM-5 includes criteria for classifying a substance use disorder as mild, moderate or severe. In some embodiments of the methods disclosed herein, the substance use disorder is selected from a mild substance use disorder, a moderate substance use disorder or a severe substance use disorder. In some embodiments, the substance use disorder is a mild substance use disorder. In some embodiments, the substance use disorder is a moderate substance use disorder. In some embodiments, the substance use disorder is a severe substance use disorder.

Anxiety and depression are highly prevalent co-morbid disorders in patients undergoing treatment of substance use or substance abuse.

The compounds of the present disclosure may have anxiolytic properties ameliorating the need for treatment of a patient with an anxiolytic agent where said patients suffers from co-morbid anxiety. Thus, in some embodiments, the present disclosure provides a method according to Method 1, or any of Methods 1.1-1.24, wherein the central nervous system disorder is a substance addiction, substance use disorders and/or substance-induced disorders, or a substance abuse disorder, for example, in a patient suffering from symptoms of anxiety or who is diagnosed with anxiety as a co-morbid disorder, or as a residual disorder, wherein the method does not comprise the further administration of an anxiolytic agent, such as a benzodiazepine. Benzodiazepines are GABA-modulating compounds, including those discussed with reference to Method 3.1 and 3.2 below.

In another embodiment of the third aspect, the present disclosure provides Method 1 or any of Methods 1.1-1.24, wherein the method is further as described as follows:

1.25 Method 1 or any of Methods 1.1-1.24, wherein the central nervous system disorder is a disorder selected from obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, tic disorders (including transient tic disorders, chronic tic disorders, motor tic disorders and verbal tic disorders, e.g., Tourette's syndrome), attention deficit-hyperactivity disorder (ADHD), attention deficit disorder (ADD), impulse control disorder, and related disorders, and combination thereof.

1.26 Method 1 or any one Method 1.1-1.24, wherein the central nervous system disorder is selected from obsessive-compulsive disorder (OCD), obsessive-compulsive personality disorder (OCPD), social anxiety disorder, panic disorder, agoraphobia, compulsive gambling disorder, compulsive eating disorder, body dysmorphic disorder and impulse control disorder.

1.27 Method 1 or any one of Method 1.1-1.24, wherein the central nervous system disorder is obsessive-compulsive disorder (OCD) or obsessive-compulsive personality disorder (OCPD).

1.28 Any foregoing method, wherein said patient is not responsive to or cannot tolerate the side effects from, treatment with selective serotonin reuptake inhibitors (SSRIs), such as citalopram, escitalopram, fluoxetine, fluvoxamine, paroxetine, and sertraline.

1.29 Any foregoing method, wherein said patient is not responsive to or cannot tolerate the side effects from, treatment with serotonin-norepinephrine reuptake inhibitors (SNRIs), such as venlafaxine, sibutramine, duloxetine, atomoxetine, desvenlafaxine, milnacipran, and levomilnacipran.

1.30 Any foregoing method, wherein said patient is not responsive to or cannot tolerate the side effects from, treatment with antipsychotic agents, such as clomipramine, risperidone, quetiapine and olanzapine.

1.31 Method I or any of Methods 1.1-1.30, wherein the central nervous system disease or disorder is a drug dependency (for example, stimulant dependency (i.e., stimulant use disorder), cocaine dependency, or amphetamine dependency), and wherein the patient also suffers from a co-morbidity, such as anxiety, depression or psychosis; optionally wherein the patient also suffers from an opiate overdose;

1.32 Method I or any of Methods 1.1-1.31, wherein the central nervous system disorder is a pain disorder, e.g., a condition associated with pain, such as cephalic pain, idiopathic pain, neuropathic pain, chronic pain (e.g., moderate to moderately severe chronic pain, for example, in patients requiring 24-hour extended treatment for other ailments), fibromyalgia, dental pain, traumatic pain, or chronic fatigue;

1.33 Any of the foregoing methods, wherein the patient is not responsive to or cannot tolerate the side effects of non-narcotic analgesics and/or opiate and opioid drugs, or wherein the use of opiate drugs are contraindicated in said patient, for example, due to prior substance abuse or a high potential for substance abuse, such as opiate and opioid drugs including, e.g., morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentantyl, alfentanyl, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, and anileridine, or any combinations thereof;

1.34 Any of the foregoing methods, wherein the effective amount is 1 mg-1000 mg, preferably 2.5 mg-50 mg, or for a long-acting formulation, 25 mg-1500 mg, for example, 50 mg to 500 mg, or 250 mg to 1000 mg, or 250 mg to 750 mg, or 75 mg to 300 mg;

1.35 Any of the foregoing methods, wherein the effective amount is 1 mg-100 mg per day, preferably 2.5 mg-50 mg per day.

In still another embodiment, the present disclosure provides any of the Methods 1 or 1.1-1.35 as hereinbefore described wherein the disorder is schizophrenia or sleep disorder. In some embodiments, said schizophrenia is associated with depression. In some embodiments, the sleep disorder is a sleep maintenance disorder, such as sleep maintenance insomnia.

In still another embodiment, the present disclosure provides any of Methods 1.1-1.35, wherein the Pharmaceutical Composition is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In still another embodiment, the invention provides any Method 1 or 1.1-1.35 as hereinbefore described, wherein the Depot Composition of the present disclosure is administered for controlled- and/or sustained-release of the Compounds of the Invention over a period of time.

In a fourth aspect, the invention provides a method (Method 2) for the prophylaxis or treatment of one or more sleep disorders comprising administering to a patient in need thereof a Compound of Formula I et seq. or a Pharmaceutical Composition I, I-A, I-B, I-C, or any of P.1-P.7. In particular embodiments, Method 1 comprises administering:

2.1. Compound I or any of 1.1-1.8, in free form;
2.2. Compound I or any of 1.1-1.8, in pharmaceutically acceptable salt form;
2.3. Compound I or any of 1.1-1.8, in acid addition salt form;
2.4. Pharmaceutical Composition I;
2.5. Any of Pharmaceutical Compositions I-A, I-B or I-C;
2.6. Any of Pharmaceutical Composition P.1 to P.7; or
2.7. Any Osmotic-controlled Release Oral Delivery System Composition as hereinbefore described.

In a further embodiment of the fourth aspect, the invention provides Method 2, or 2.1-2.7, wherein the sleep disorder includes sleep maintenance insomnia, frequent awakenings, and waking up feeling unrefreshed; for example:

2.8 Any of the foregoing methods, wherein the sleep disorder is sleep maintenance insomnia;
2.9 Any of the foregoing methods, wherein the effective amount is 1 mg-5 mg, preferably 2.5-5 mg, per day;
2.10 Any of the foregoing methods, wherein the effective amount is 2.5 mg or 5 mg, per day;
2.11 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;
2.12 Any of the foregoing methods wherein the patient suffers from Parkinson's disease.

In a further embodiment of the fourth aspect, the invention provides Method 2, or any of 2.1-2.12, wherein the sleep disorder includes sleep maintenance insomnia, frequent awakenings, and waking up feeling unrefreshed.

The Compounds of the present disclosure and the Pharmaceutical Compositions of the present disclosure may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the present disclosure may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of the present disclosure in combination with one or more second therapeutic agents in free or salt form (e.g., pharmaceutically acceptable salt form), wherein the dosages of (i) the second therapeutic agent(s) or (ii) both Compound of the present disclosure and the second therapeutic agents, are lower than if the agents/compounds are administered as a monotherapy. In a particular embodiment, the Compounds of the present disclosure are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

In some further embodiments of the present disclosure, the Pharmaceutical Compositions of the present disclosure may be used in combination with a second therapeutic agent, particularly at lower dosages than when the individual agents are used as a monotherapy so as to enhance the therapeutic activities of the combined agents without causing the undesirable side effects, wherein the second therapeutic agent is an opiate antagonist or inverse agonist (e.g., naloxone). The Compounds of the present disclosure may be simultaneously, sequentially, or contemporaneously administered with such opiate antagonists or opiate inverse agonists.

Therefore, in an fifth aspect, the present disclosure provides Method 1, or any of Methods 1.1-1.35, or Method 2 or any of 2.1-2.12, further comprising the administration of one or more therapeutic agents to the patient, wherein the one or more therapeutic agents are selected from compounds that modulate GABA activity (e.g., enhances the activity and facilitates GABA transmission), a GABA-B agonist, a 5-HT receptor modulator (e.g., a $5\text{-}HT_{1A}$ agonist, a $5\text{-}HT_{2A}$ antagonist, a $5\text{-}HT_{2A}$ inverse agonist, etc.), a melatonin receptor agonist, an ion channel modulator (e.g., blocker), a serotonin-2 receptor antagonist/reuptake inhibitor (e.g., a compound having both $5\text{-}HT_2$ antagonism and serotonin reuptake inhibition, i.e., SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and opiate agonist and/or partial opiate agonist (such as a mu-, kappa- or delta-opiate receptor agonist or partial agonist), or opiate antagonist or inverse agonist (such as mu-, kappa- or delta-opiate receptor antagonist or inverse agonist), nociceptin agonist, and an antipsychotic agent, e.g., an atypical antipsychotic agent, in free or pharmaceutically acceptable salt form (Method 1-A and 2-A respectively; collectively, "Method 3"). In further embodiments of the eighth aspect, the present disclosure provides Method 1, or any of Methods 1.1-1.35, or Method 2 or any of 2.1-2.12, further comprising the administration to the patient of one or more therapeutic agents selected from the foregoing and further selected from agonists or partial agonists or antagonists or inverse agonists of the mu-opiate, kappa-opiate, delta-opiate, and/or nociceptin/orphanin receptors. In further embodiments of the tenth aspect, the present disclosure also provides Method 1, or any of Methods 1.1-35, or Method 2 or any of 2.1-2.12, further comprising the administration to the patient of one or more therapeutic agents selected from a serotonin $5\text{-}HT_6$ receptor antagonist, and an mGluR-2, -3 or -5 receptor agonist or antagonist (including both positive and negative modulators and partial agonists).

In a further embodiment of the fifth aspect, the invention provides Method 3 (i.e., Method 1-A or 2-A), further comprising the administration to the patient of one or more therapeutic agents, as follows:

3.1 Method 1-A or 2-A, wherein the therapeutic agent(s) is compounds that modulate GABA activity (e.g., enhances the activity and facilitates GABA transmission);

3.2 Method 1-A or 2-A or 3.1, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals) and estazolam;

3.3 Method 1-A or 2-A, wherein the therapeutic agent is an additional $5HT_{2A}$ receptor antagonist;

3.4 Method 1-A or 2-A or 3.3, wherein said additional $5HT_{2A}$ receptor antagonist is selected from one or more of pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), and AVE8488 (Sanofi-Aventis, France);

3.5 Method 1-A or 2-A, wherein the therapeutic agent is a melatonin receptor agonist;

3.6 Method 1-A or 2-A or 3.5, wherein the melatonin receptor agonist is selected from a group consisting of one or more of melatonin, ramelteon (ROZEREM®, Takeda Pharmaceuticals, Japan), VEC-162 (Vanda Pharmaceuticals, Rockville, MD), PD-6735 (Phase II Discovery) and agomelatine;

3.7 Method 1-A or 2-A, wherein the therapeutic agent is an ion channel blocker;

3.8 Method I-A or 2-A or 3.7, wherein said ion channel blocker is one or more of lamotrigine, gabapentin and pregabalin.

3.9 Method 1-A or 2-A, wherein the therapeutic agent is an orexin receptor antagonist;

3.10 Method 1-A or 2-A or 3.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

3.11 Method 1-A or 2-A, wherein the therapeutic agent is the serotonin-2 receptor antagonist/reuptake inhibitor (SARI);

3.12 Method 1-A or 2-A or 3.11, wherein the serotonin-2 receptor antagonist/reuptake inhibitor (SARI) is selected from a group consisting of one or more Org 50081 (Organon-Netherlands), ritanserin, nefazodone, serzone and trazodone;

3.13 Method 1-A or 2-A, wherein the therapeutic agent is the $5HT_{1A}$ agonist;

3.14 Method 1-A or 2-A or 3.13, wherein the $5HT_{1A}$ agonist is selected from a group consisting of one or more of repinotan, sarizotan, eptapirone, buspirone and MN-305 (MediciNova, San Diego, CA);

3.15 Method 1-A or 2-A, wherein the therapeutic agent is the neurokinin-1 drug;

3.16 Method 1-A or 2-A or 3.15, wherein the neurokinin-1 drug is Casopitant (GlaxoSmithKline);

3.17 Method 1-A or 2-A, wherein the therapeutic agent is an antipsychotic agent;

3.18 Method 1-A or 2-A or 3.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone and paliperidone;

3.19 Method 1-A or 2-A, wherein the therapeutic agent is an anti-depressant;

3.20 Method 1-A or 2-A or 3.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, and venlafaxine;

3.21 Method 1-A or 2-A, 3.17 or 3.18, wherein the antipsychotic agent is an atypical antipsychotic agent;

3.22 Method 1-A or 2-A, or any of 3.17-3.21, wherein the atypical antipsychotic agent is selected from a group consisting of brexpiprazole, cariprazine, asenapine, lurasidone, clozapine, aripiprazole, olanzapine, quetiapine, risperidone, ziprasidone, and paliperidone;

3.23 Method 1-A or 2-A, wherein the therapeutic agent is selected from any of methods 3.1-3.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam, pimavanserin, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), AVE8488 (Sanofi-Aventis, France), repinotan, sarizotan, eptapirone, buspirone, MN-305 (MediciNova, San Diego, CA), melatonin, ramelteon (ROZEREM®, Takeda Pharmaceuticals, Japan), VEC-162 (Vanda Pharmaceuticals, Rockville, MD), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine, molindone, perphenazine, pimozide, prochlorperazine promazine, thioridazine, thiothixene, trifluoperazine, brexpiprazole, cariprazine, asenapine, lurasidone, clozapine, aripiprazole, olanzapine, quetiapine, risperidone, ziprasidone and paliperidone;

3.24 Method 1-A or 2-A, wherein the therapeutic agent is an H3 agonist;

3.25 Method 1-A or 2-A, wherein the therapeutic agent is an H3 antagonist;

3.26 Method 1-A or 2-A, wherein the therapeutic agent is a noradrenergic agonist or antagonist;

3.27 Method 1-A or 2-A, wherein the therapeutic agent is a galanin agonist;

3.28 Method 1-A or 2-A, wherein the therapeutic agent is a CRH antagonist;

3.29 Method 1-A or 2-A, wherein the therapeutic agent is a human growth hormone;

3.30 Method 1-A or 2-A, wherein the therapeutic agent is a growth hormone agonist;

3.31 Method 1-A or 2-A, wherein the therapeutic agent is estrogen;

3.32 Method 1-A or 2-A, wherein the therapeutic agent is an estrogen agonist;

3.33 Method 1-A or 2-A, wherein the therapeutic agent is a neurokinin-1 drug;

3.34 Method 1-A or 2-A, wherein a therapeutic agent is combined with compounds of Formula I et seq., and the therapeutic agent is an anti-Parkinson agent such as L-dopa, co-careldopa, duodopa, stalevo, Symmetrel, benztropine, biperiden, bromocriptine, entacapone, pergolide, pramipexole, procyclidine, ropinirole, selegiline and tolcapone;

3.35 Method 1-A or 2-A, wherein the therapeutic agent is an opiate agonist or partial opiate agonist, for example, a mu-agonist or partial agonist, or a kappa-agonist or partial agonist, including mixed agonist/antagonists (e.g., an agent with partial mu-agonist activity and kappa-antagonist activity);

3.36 Method 3.35, wherein the therapeutic agent is buprenorphine, optionally, wherein said method does not include co-treatment with an anxiolytic agent, e.g., a GABA compound or benzodiazepine;

3.37 Method 1-A or 2-A, wherein compounds of Formula I may be used to treat sleep disorders, depression, psychosis, or any combinations thereof, in patients suffering from the listed diseases and/or Parkinson's disease;

3.38 Method 1-A or 2-A, wherein the disorder is selected from at least one or more of psychosis, e.g., schizophrenia, depression, mood disorders, sleep disorders (e.g., sleep maintenance and/or sleep onset) or any combination of disorders thereof;

3.39 Method 1-A or 2-A, wherein the therapeutic agent(s) is an opiate receptor antagonist or inverse agonist, e.g., a full opiate antagonist, for example, selected from naloxone, naltrexone, nalmefene, methadone, nalorphine, levallorphan, samidorphan, nalodeine, cyprodime, or norbinaltorphimine;

3.40 Any of the foregoing methods wherein the disorder is sleep disorder;

3.41 Any of the foregoing methods, wherein the disorder is sleep disorder associated with psychosis, e.g., schizophrenia or Parkinson's disease; in free or pharmaceutically acceptable salt form.

In a sixth aspect of the invention, the combination of a Compound of the present disclosure and one or more second therapeutic agents as described in Methods 1-A, 2-A or any of Methods 3 or 3.1-3.41 may be administered to the patient as a single Pharmaceutical Composition, such as a depot composition, as hereinbefore described. The combination compositions may include mixtures of the combined drugs, as well as two or more separate compositions of the drugs, which individual compositions can be, for example, co-administered together to a patient.

In a particular embodiment, Methods 1-A, 2-A, 3 or 3.1-3.41 comprises administering to the patient in need thereof, a Compound of the Invention in combination with an atypical antipsychotic agent, e.g., a compound selected from brexpiprazole, cariprazine, asenapine, lurasidone, clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods 1-A, 2-A, 3 or 3.1-3.41 comprises administering to the patient in need thereof, a Compound of the Invention in combination with an antidepressant, e.g., amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compound of the Invention.

In still another embodiment, Methods 1-A, 2-A, 3 or 3.1-3.41 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam or any combinations thereof, in free or pharmaceutically acceptable salt form. In other embodiments, the methods disclosed herein do not further comprise administration of an GABA compound, a benzodiazepine or any other anxiolytic agent.

In another preferred embodiment, Methods 1-A, 2-A, 3 or 3.1-3.41 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods 1-A, 2-A, 3 or 3.1-3.41 comprises administering to a patient in need thereof, a Compound of the Invention in combination (including as part of a daily dosage regimen) with an atypical stimulant, e.g., a modafinil, adrafinil, or armodafinil. A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In another embodiment, Methods 1-A, 2-A, 3 or 3.1-3.41 comprises administering to a patient in need thereof, a Compound of the Invention in combination (including as part of a daily dosage regimen) with an opiate receptor antagonist or inverse agonist, e.g., a full opiate antagonist, for example, selected from naloxone, naltrexone, nalmefene, methadone, nalorphine, levallorphan, samidorphan, nalodeine, cyprodime, or norbinaltorphimine.

In a sixth aspect, the invention provides use of a compound or composition as described in the following:

6.1. Compound I or any of 1.1-1.8, in free form;
6.2. Compound I or any of 1.1-1.8, in pharmaceutically acceptable salt form;
6.3. Compound I or any of 1.1-1.8, in acid addition salt form;
6.4. Pharmaceutical Composition I;
6.5. Any of Pharmaceutical Compositions I-A, I-B or I-C;
6.6. Any of Pharmaceutical Composition P.1 to P.7; or
6.7. Any Osmotic-controlled Release Oral Delivery System Composition as hereinbefore described;

(in the manufacture of a medicament) for the treatment or prophylaxis of one or more disorders as disclosed hereinbefore, e.g., in any of Method 1 or 1.1-1.35, any of Method 2 and 2.1-2.12, Methods I-A, II-A, and Method 3 or 3.3-3.41, or in any other methods described herein.

DETAILED DESCRIPTION

If not otherwise specified or clear from context, the following terms as used herein have the following meetings.

The term "pharmaceutically acceptable diluent or carrier" is intended to mean diluents and carriers that are useful in pharmaceutical preparations, and that are free of substances that are allergenic, pyrogenic or pathogenic, and that are known to potentially cause or promote illness. Pharmaceutically acceptable diluents or carriers thus exclude bodily fluids such as example blood, urine, spinal fluid, saliva, and the like, as well as their constituent components such as blood cells and circulating proteins. Suitable pharmaceutically acceptable diluents and carriers can be found in any of several well-known treatises on pharmaceutical formulations, for example Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; and Martindale, The Extra Pharmacopoeia, Thirty-Second Edition (The Pharmaceutical Press, London, 1999); all of which are incorporated by reference herein in their entirety.

The terms "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization, LC-MS and LC-MS/MS techniques and the like), in sufficient purity to be characterizable by standard analytical techniques described herein or well known to the skilled artisan.

Unless otherwise indicated, the Compounds of the present disclosure, e.g., Compound I or 1.1-1.8 (collectively, Compounds of Formulas I et seq.) may exist in free base form or in salt form, such as a pharmaceutically acceptable salt form, e.g., as acid addition salts. An acid-addition salt of a compound of the invention which is sufficiently basic, for example, an acid-addition salt with, for example, an inorganic or organic acid, for example hydrochloric acid or toluenesulfonic acid. In addition, a salt of a compound of the invention which is sufficiently acidic is an alkali metal salt, for example a sodium or potassium salt, or a salt with an organic base which affords a physiologically-acceptable cation. In a particular embodiment, the salt of the Compounds of the Invention is a toluenesulfonic acid addition salt.

The Compounds of the present disclosure are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included within the scope of the compounds of the present disclosure.

The compound of Formula I may be in pure, or substantially pure, enantiomeric form, e.g., greater than 70% enantiomeric excess ("ee"), preferably greater than 80% ee, more preferably greater than 90% ee, most preferably greater than 95% ee. Compounds of the present disclosure are to be understood as embracing mixtures comprising some quantity of the enantiomer of the compound of Formula I, as well as diastereomeric mixtures thereof. The purification of said isomers and the separation of said isomeric mixtures may be accomplished by standard techniques known in the art (e.g., column chromatography, preparative TLC, preparative HPLC, simulated moving bed and the like).

It is also intended that the compounds of the present disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the compounds of the disclosure may be replaced with deuterium (a stable isotope which is non-radioactive). Examples of known stable isotopes include, but not limited to, deuterium ($^2$H or D), $^{13}$C, $^{15}$N, $^{18}$O. Alternatively, unstable isotopes, which are radioactive isotopes which contain additional neutrons compared to the abundant nuclides of the same species (i.e., element), e.g., $^{123}$I, $^{131}$I, $^{125}$I, $^{11}$C, $^{18}$F, may replace the corresponding abundant species of I, C and F. Another example of useful isotope of the compound of the invention is the $^{11}$C isotope. These radio isotopes are useful for radio-imaging and/or pharmacokinetic studies of the compounds of the invention. In addition, the substitution of atoms of having the natural isotopic distributing with heavier isotopes can result in desirable change in pharmacokinetic rates when these substitutions are made at metabolically liable sites. For example, the incorporation of deuterium ($^2$H) in place of hydrogen can slow metabolic degradation when the position of the hydrogen is a site of enzymatic or metabolic activity.

Compounds of the present disclosure may be included as a depot formulation, e.g., by dispersing, dissolving or encapsulating the Compounds of the Invention in a polymeric matrix as described hereinbefore, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), co-polyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e.g., glucose or, e.g., mannitol. These esters are known and described in GB 2,145,422 and in U.S. Pat. No. 5,538,739, the contents of which are incorporated by reference.

The star polymers may be prepared using polyhydroxy compounds, e. g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d, l-lactide-co-glycolide) have a central glucose moiety having rays of linear polylactide chains.

The depot compositions of the invention (e.g., Compositions 6 and 6.1-6.10, in a polymer matrix) as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the present disclosure incorporated in the microparticles usually ranges from about 1 wt % to about 90 wt. %, preferably 30 to 50 wt. %, more preferably 35 to 40 wt. %. By weight % is meant parts of the Compounds of the present disclosure per total weight of microparticle.

The pharmaceutical depot compositions may comprise a pharmaceutically-acceptable diluent or carrier, such as a water miscible diluent or carrier.

Details of Osmotic-controlled Release Oral Delivery System composition may be found in EP 1 539 115 (U.S. Pub. No. 2009/0202631) and WO 2000/35419 (US 2001/0036472), the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, parenterally (intravenously, intramuscular or subcutaneous) or transdermally. In certain embodiments, the Compounds of the Invention, e.g., in depot formulation, is preferably administered parenterally, e.g., by injection, for example, intramuscular or subcutaneous injection.

In general, satisfactory results for Method 1 and 1.1-1.35, Method 2 and 2.1-2.12, and Method 3 and 3.1-3.41, or use of the Compounds of the present disclosure as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; (4) sleep disorders associated with psychosis, e.g., schizophrenia, or Parkinson's disease; and (5) substance addiction, substance use disorders and/or substance-induced disorders, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration.

Satisfactory results for Method 2 or 2.1-2.12 or use of the Compounds of the present disclosure as hereinbefore described, e.g. for the treatment of sleep disorder alone are indicated to be obtained on oral administration at dosages of the order from about 2.5 mg-5 mg, e.g., 2.5 mg, 3 mg, 4 mg or 5 mg, of a Compound of the Invention, in free or pharmaceutically acceptable salt form, once daily, preferably via oral administration.

Satisfactory results for Method 1-A or Method 2-A, or any of 3.1-3.41 are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 3.1-3.41 are indicated to be obtained at less than 5 mg, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. Duration of action of the Compounds of the present disclosure may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the present disclosure can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069 (each equivalent to US 2011/112105).

Pharmaceutical compositions comprising Compounds of the present disclosure may be prepared using conventional diluents or excipients (an example include, but is not limited to sesame oil) and techniques known in the galenic art. Thus, oral dosage forms may include tablets, capsules, solutions, suspensions and the like.

The term "concurrently" when referring to a therapeutic use means administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration Methods of Making the Compounds of the Invention The Compound of Formula A, which is the enantiomer of the Compound of Formula I, and methods for its synthesis, have been disclosed in US 2017/319580. The synthesis of similar fused gamma-carbolines has been disclosed in, for example, U.S. Pat. Nos. 8,309,722, 8,993,572, U.S. 2017/0183350, WO 2018/126140 and WO 2018/126143, the contents of each of which are incorporated by reference in their entireties. Compounds of the present disclosure can be prepared using similar procedures, wherein the opposite enantiomer of the compound of Formula I, or of its synthetic intermediates, is isolated and purified.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

Salts of the Compounds of the present disclosure may be prepared as similarly described in U.S. Pat. Nos. 6,548,493; 7,238,690; 6,552,017; 6,713,471; 7,183,282; 8,648,077; 9,199,995; 9,586,860; U.S. RE39680; and U.S. RE39679, the contents of each of which are incorporated by reference in their entirety.

EXAMPLES

Example 1: Synthesis of (6bS,10aR)-8-(3-(4-fluorophenoxy)propyl)-6b,7,8,9,10,10a-hexahydro-1H-pyrido[3',4':4,5]pyrrolo[1,2,3-de]quinoxalin-2(3H)-one

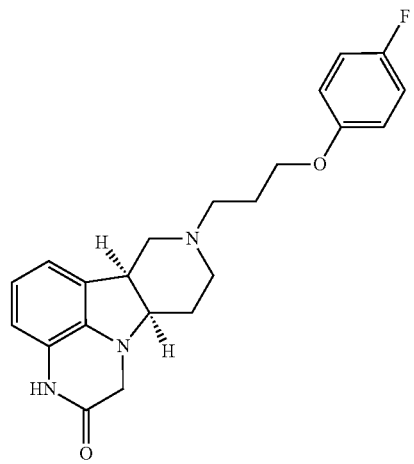 [SMILES: O=C1CN2c3c(cccc3[C@H]3CN(CCCOc4ccc(F)cc4)CC[C@H]32)N1]

Step 1: A degassed suspension of (4aR,9bS)-ethyl 6-bromo-3,4,4a,5-tetrahydro-1H-pyrido[4,3-b]indole-2(9bH)-carboxylate (21.5 g, 66.2 mmol), chloroacetamide (18 g, 198 mmol), and KI (36 g, 198 mmol) in dioxane (80 mL) is stirred at 105° C. for 24 h. The solvent is removed and the residue is suspended in dichloromethane (200 mL) and extracted with water (100 mL). The separated dichloromethane phase is dried over $Mg_2SO_4$ for 1 h and then filtered. The filtrate is evaporated to give a crude product as a brown oil. To the brown oil is added ethyl acetate (100 m L) and the mixture is sonicated for 2 min. A yellow solid gradually precipitates from the mixture, which turns into a gel after standing at room temperature for additional 2 h. Additional ethyl acetate (10 mL) is added and the resulting solid is filtered. The filtered cake is rinsed with ethyl acetate (2 m L) and further dried under high vacuum. The product (4aR,9bS)-ethyl 5-(2-amino-2-oxoethyl)-6-bromo-3,4,4a,5-tetrahydro-1H-pyrido[4,3-b]indole-2(9bH)-carboxylate is obtained as an off white solid (25.8 g, yield 100%). MS (ESI) m/z 382.0 [M+H]$^+$. This product is used directly in the next step without further purification.

Step 2: A mixture of (4aR,9bS)-ethyl 5-(2-amino-2-oxoethyl)-6-bromo-3,4,4a,5-tetrahydro-1H-pyrido[4,3-b]indole-2(9bH)-carboxylate (15 g, 39.2 mmol), $K_2CO_3$ (14.2 g, 86.2 mmol), CuI (1.5 g, 7.8 mmol) in dioxane (50 mL) is bubbled with argon for 5 min. To this mixture is added N,N,N',N'-tetramethylethylenediamine (3.7 mL) and the resulting suspension is stirred at 100° C. for 48 h. The reaction mixture is cooled to room temperature and poured onto a silica gel pad to filter. The filtered cake is rinsed with ethyl acetate (1.5 L). The combined filtrate is concentrated to dryness to give a product (6bS,10aR)-ethyl 2-oxo-2,3,6b,7,10,10a-hexahydro-1H-pyrido [3',4':4,5]pyrrolo[1,2,3-de]quinoxaline-8(9H)-carboxylate as a white solid (3.5 g, yield 30%). MS (ESI) m/z 302.1 [M+H]+. This product is used directly in the next step without further purification.

Step 3: (6bS,10aR)-ethyl 2-oxo-2,3,6b,7,10,10a-hexahydro-1H-pyrido [3',4':4,5]pyrrolo[1,2,3-de]quinoxaline-8(9H)-carboxylate (3.5 g, 11.6 mmol) is suspended in HBr acetic acid solution (30 mL, 33% w/w) at room temperature. The mixture is heated at 70° C. for 2 h. After cooling and treatment with ethyl acetate (150 mL), the mixture is filtered. The filter cake is washed with ethyl acetate (5 mL), and then dried under high vacuum. The obtained HBr salt is then suspended in methanol (40 mL) and cooled with dry ice in isopropanol. Under vigorous stirring, ammonia solution (20 mL, 7 N in methanol) is slowly added to the suspension to adjust the pH of the mixture to 14. The obtained mixture is dried under high vacuum to give a crude product (6bS,10aR)-6b,7,8,9,10,10a-hexahydro-1H-pyrido[3',4':4,5]pyrrolo[1,2,3-de]quinoxalin-2(3H)-one HBr salt (7.8 g). MS (ESI) m/z 230.2 [M+H]$^+$. This product is used directly in the next step without further purification.

Step 4: A mixture (6bS,10aR)-6b,7,8,9,10,10a-hexahydro-1H-pyrido[3',4':4,5]pyrrolo[1,2,3-de]quinoxalin-2(3H)-one HBr salt (1.0 g, 4.4 mmol as a pure starting material), 1-(3-chloroproxy)-4-fluorobenzene (1.4 mL, 8.8 mmol) and KI (1.45 g, 8.7 mmol) in DMF (15 mL) is bubbled with argon for 3 minutes and DIPEA (1.5 mL, 8.7 mmol) is added. The resulting mixture is heated to 76° C. and stirred at this temperature for 2 h. The solvent is removed, and to the residue water (80 mL) is added. The resulting mixture is extracted with DCM (100 mL). The DCM phase is dried over $K_2CO_3$ and concentrated to dryness. The residue is purified by silica gel column chromatography using a gradient of 0-100% mixed solvents [ethyl acetate/methanol/7N $NH_3$ (10:1:0.1 v/v)] in ethyl acetate to obtain the title product (6bS,10aR)-8-(3-(4-fluorophenoxy)propyl)-6b,7,8,9,10,10a-hexahydro-1H-pyrido[3',4':4,5]pyrrolo[1,2,3-de]quinoxa-lin-2(3H)-one as an off-white solid (650 mg, yield 25%). MS (ESI) m/z 382.2 [M+1]$^+$. $^1$H NMR (500 MHz, DMSO-d$_6$) δ 10.34 (s, 1H), 7.10 (t, J=8.8 Hz, 2H), 6.97-6.88 (m, 2H), 6.77 (d, J=7.3 Hz, 1H), 6.64 (t, J=7.6 Hz, 1H), 6.58 (dd, J=7.8, 1.0 Hz, 1H), 3.97 (t, J=6.4 Hz, 2H), 3.80 (d, J=14.5 Hz, 1H), 3.31 (m, 1H), 3.28-3.24 (m, 1H), 3.21 (dt, J=10.8, 6.4 Hz, 1H), 2.92-2.82 (m, 1H), 2.68-2.60 (m, 1H), 2.46-2.29 (m, 2H), 2.09 (td, J=11.6, 2.7 Hz, 1H), 1.94 (dd, J=14.7, 2.8 Hz, 1H), 1.90-1.73 (m, 3H), 1.67 (t, J=11.0 Hz, 1H).

Example 2: Receptor Binding Profile

Receptor binding is determined for the Compounds of Example 1 and of Formulas A and B. The following literature procedures are used, each of which reference is incorporated herein by reference in their entireties: 5-HT$_{2A}$: Bryant, H. U. et al. (1996), *Life Sci.*, 15:1259-1268; D2: Hall, D. A. and Strange, P. G. (1997), *Brit. J. Pharmacol.*, 121:731-736; D1: Zhou, Q. Y. et al. (1990), *Nature*, 347: 76-80; SERT: Park, Y. M. et al. (1999), *Anal. Biochem.*, 269:94-104; Mu opiate receptor: Wang, J. B. et al. (1994), *FEBS Lett.*, 338:217-222.

In general, the results are expressed as a percent of control specific binding:

$$\frac{\text{measured specific binding}}{\text{control specific binding}} \times 100$$

and as a percent inhibition of control specific binding:

$$100 - \left(\frac{\text{measured specific binding}}{\text{control specific binding}} \times 100\right)$$

obtained in the presence of the test compounds.

The IC$_{50}$ values (concentration causing a half-maximal inhibition of control specific binding) and Hill coefficients (nH) are determined by non-linear regression analysis of the competition curves generated with mean replicate values using Hill equation curve fitting:

$$Y = D + \left[\frac{A-D}{1+(C/C_{50})^{nH}}\right]$$

where Y=specific binding, A=left asymptote of the curve, D=right asymptote of the curve, C=compound concentration, C$_{50}$=IC$_{50}$, and nH=slope factor. This analysis was performed using in-house software and validated by comparison with data generated by the commercial software SigmaPlot® 4.0 for Windows® (© 1997 by SPSS Inc.). The inhibition constants (Ki) were calculated using the Cheng Prusoff equation:

$$Ki = \frac{IC_{50}}{(1+L/K_D)}$$

where L=concentration of radioligand in the assay, and K$_D$=affinity of the radioligand for the receptor. A Scatchard plot is used to determine the K$_D$.

The following receptor affinity results are obtained:

| Receptor | Ki (nM) or maximum inhibition | |
|---|---|---|
| | Compound A | Ex. 1 |
| 5-HT$_{2A}$ | 8.3 | 105 |
| D2 | 160 | 208 |
| D1 | 50 | 75 |
| SERT | 590 | NI @ 100 nM |
| Mu opiate receptor | 11 | 292 |

These receptor binding studies demonstrate the unexpectedly different pharmacologic profile of the compound of Example 1 (the compound of Formula I) in comparison to its enantiomer, the compound of Formula A.

What is claimed:

1. A compound of a Formula I:

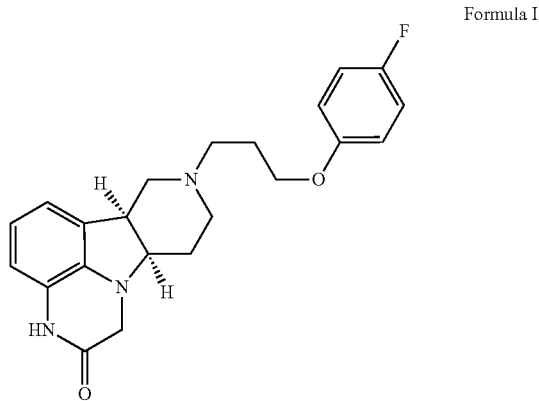 [SMILES: O=C1CN2c3c(cccc3[C@H]3CN(CCCOc4ccc(F)cc4)CC[C@H]32)N1]

Formula I in free or pharmaceutically acceptable salt form; and
wherein the compound is in isolated and purified form of at least 90% purity.

2. The compound according to claim 1 in the form of a pharmaceutically acceptable salt.

3. A pharmaceutical composition comprising a compound according to claim 1, in free or pharmaceutically acceptable salt form, in admixture with a pharmaceutically acceptable diluent or carrier.

4. A method for the treatment or prophylaxis of a central nervous system disorder, comprising administering to a patient in need thereof a compound according to claim 1, in free or pharmaceutically acceptable salt form.

5. The method according to claim 4, wherein said disorder is selected from the group consisting of obesity, anxiety, depression, psychosis, schizophrenia, sleep disorders, sexual disorders, agoraphobia, social phobias, agitation in dementia, agitation in autism, dementia, mood disorders, substance use disorder and/or substance abuse disorder, drug dependencies, co-morbidities associated with drug dependencies, binge eating disorder, obsessive-compulsive disorder (OCD), obsessive-compulsive personality disorder (OCPD); and stimulant use disorder (SUD).

6. The method according to claim 4, wherein said disorder is a disorder involving the serotonin 5-HT$_{2A}$, serotonin reuptake transporter (SERT), dopamine D1 and/or D2 pathways.

7. The method according to claim 4, wherein said disorder is a disorder selected from the following: (1) psychosis, in a patient suffering from depression; (2) depression in a patient suffering from psychosis; (3) mood disorders associated with psychosis; (4) sleep disorders associated with psychosis; and (5) substance addiction, substance use disorders and/or substance-induced disorders.

8. The method according to claim 4, wherein said central nervous system disorder is a disorder selected from obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, attention deficit-hyperactivity disorder (ADHD), attention deficit disorder (ADD), impulse control disorder, and combination thereof.

9. The compound according to claim 1, wherein the compound is in solid crystal form.

10. The compound according to claim 1, wherein the compound has a diastereomeric excess greater than 90%.

11. The compound according to claim 10, wherein the compound is in isolated or purified form of at least 98% purity.

12. The compound according to claim 2, wherein the pharmaceutically acceptable salt is a hydrochloric or toluenesulfonic acid salt.

13. The method according to claim 5, wherein said disorder is selected from the group consisting of general anxiety, social anxiety, panic disorders, refractory depression, major depressive disorder, psychosis associated with dementia, agitation in Alzheimer's disease, dementia of Alzheimer's disease, dementia of Parkinson's disease, cocaine dependency, amphetamine dependency, and withdrawal from drug dependency.

14. The compound according to claim 1, wherein the compound has an enantiomeric excess greater than 90%.

* * * * *